(12) United States Patent
Navarrini

(10) Patent No.: US 6,963,013 B2
(45) Date of Patent: Nov. 8, 2005

(54) METHOD OF MAKING FLUOROVINYL ETHERS AND POLYMERS OBTAINABLE THEREFROM

(75) Inventor: Walter Navarrini, Milan (IT)

(73) Assignee: Solvay Solexis Sp.A., Milan (IT)

( * ) Notice: Subject to any disclaimer, the term of this patent is extended or adjusted under 35 U.S.C. 154(b) by 0 days.

(21) Appl. No.: 09/840,527

(22) Filed: Apr. 23, 2001

(65) Prior Publication Data

US 2001/0051753 A1 Dec. 13, 2001

(30) Foreign Application Priority Data

Apr. 21, 2000 (IT) .................................... MI2000A0902

(51) Int. Cl.$^7$ .............................................. C07C 41/05

(52) U.S. Cl. ...................... 568/615; 568/616; 568/649; 568/654; 568/674

(58) Field of Search ................................ 568/674, 615, 568/616, 654, 649

(56) References Cited

U.S. PATENT DOCUMENTS

| | | |
|---|---|---|
| 2,515,628 A | 7/1950 | Castle |
| 2,520,338 A | 8/1950 | Robertson |
| 3,085,083 A | 4/1963 | Schreyer |
| 3,132,123 A | 5/1964 | Harris et al. |
| 3,291,843 A | 12/1966 | Fritz et al. |
| 3,450,684 A | 6/1969 | Darby et al. |
| 3,635,926 A | 1/1972 | Gresham et al. |
| 3,752,787 A | 8/1973 | De Brunner et al. |
| 3,810,874 A | 5/1974 | MIlsch et al. |
| 3,817,960 A | 6/1974 | Resnick |
| 3,876,654 A | 4/1975 | Pattison |
| 3,896,179 A | 7/1975 | Resnick |
| 4,035,565 A | 7/1977 | Apotheker et al. |
| 4,233,427 A | 11/1980 | Bargain et al. |
| 4,243,770 A | 1/1981 | Tatemoto et al. |
| 4,259,463 A | 3/1981 | Moggi et al. |
| 4,287,320 A | 9/1981 | Kolb |
| 4,340,750 A | 7/1982 | Yamabe et al. |
| 4,487,903 A | 12/1984 | Tatemoto et al. |
| 4,515,989 A | 5/1985 | Ezzell et al. |
| 4,550,132 A | 10/1985 | Capriotti |
| 4,564,682 A | 1/1986 | Kussmaul et al. |
| 4,619,983 A | 10/1986 | Yamabe et al. |
| 4,683,395 A | 7/1987 | Mitsutsuka |
| 4,694,045 A | 9/1987 | Moore |
| 4,734,485 A | 3/1988 | Bartmann et al. |
| 4,745,165 A | 5/1988 | Arcella et al. |
| 4,762,891 A | 8/1988 | Albin et al. |
| 4,766,190 A | 8/1988 | Morita et al. |
| 4,789,717 A | 12/1988 | Giannetti et al. |
| 4,864,006 A | 9/1989 | Giannetti et al. |
| 4,882,390 A | 11/1989 | Kolb |
| 4,906,770 A | 3/1990 | Marchionni et al. |
| 4,912,171 A | 3/1990 | Grootaert et al. |
| 4,943,622 A | 7/1990 | Naraki et al. |
| 4,948,852 A | 8/1990 | Moore |
| 4,948,853 A | 8/1990 | Logothetis |
| 4,957,975 A | 9/1990 | Carlson et al. |
| 4,983,697 A | 1/1991 | Logothetis |
| 4,990,283 A | 2/1991 | Visca et al. |
| 5,066,123 A | 11/1991 | Tamm et al. |
| 5,144,092 A | 9/1992 | Marraccini et al. |
| 5,149,842 A | 9/1992 | Sianesi et al. |
| 5,173,553 A | 12/1992 | Albano et al. |
| 5,182,342 A | 1/1993 | Feiring et al. |
| 5,235,074 A * | 8/1993 | Navarrini et al. ........... 549/449 |
| 5,260,293 A | 11/1993 | Baker et al. |
| 5,260,392 A | 11/1993 | Arcella et al. |
| 5,262,490 A | 11/1993 | Kolb et al. |
| 5,268,405 A | 12/1993 | Ojakaar et al. |
| 5,285,002 A | 2/1994 | Grootaert |
| 5,296,617 A | 3/1994 | Navarrini et al. |
| 5,350,497 A | 9/1994 | Hung et al. |
| 5,378,782 A | 1/1995 | Grootaert |
| 5,401,818 A | 3/1995 | Oka et al. |
| 5,430,381 A | 7/1995 | Dower |
| 5,585,449 A | 12/1996 | Arcella et al. |
| 5,591,804 A | 1/1997 | Coggio et al. |
| 5,639,837 A | 6/1997 | Farnham et al. |
| 5,648,429 A | 7/1997 | Chiodini et al. |
| 5,648,430 A | 7/1997 | Chiodini et al. |
| 5,696,216 A | 12/1997 | Kruger et al. |
| 5,830,381 A | 11/1998 | Chiodini et al. |
| 5,891,974 A | 4/1999 | Saito et al. |
| 5,902,868 A | 5/1999 | Saito et al. |
| 5,910,552 A | 6/1999 | Saito et al. |
| 6,255,536 B1 * | 7/2001 | Worm et al. ................. 568/615 |

FOREIGN PATENT DOCUMENTS

| | | |
|---|---|---|
| CA | 1076298 | 4/1980 |
| CA | 1094247 | 1/1981 |
| EP | 0120462 | 10/1984 |

(Continued)

OTHER PUBLICATIONS

Maskornik, M. et al. "ECD–006 Fluoroelastomer—A high performance engineering material". Soc. Plast Eng. Tech. Pao. (1974), 20, 675–677.

(Continued)

*Primary Examiner*—Rosalynd Keys
(74) *Attorney, Agent, or Firm*—Kenyon & Kenyon

(57) ABSTRACT

A process for making fluorovinyl ethers having the formula $CFX=CXOCF_2OR$, wherein R is a $C_2$–$C_6$ linear, branched or $C_5$–$C_6$ cyclic (per)fluoroalkyl group, or a $C_2$–$C_6$ linear, branched (per)fluoro oxyalkyl group containing from one to three oxygen atoms; when R is fluoroalkyl or fluorooxyalkyl group as above defined, it can contain from 1 to 2 atoms, equal or different, selected from the following: H, Cl, Br, I; X=F, H; and homopolymers or polymers obtainable by polymerizing said Fluorovinyl ethers with at least another polymerizable monomer.

6 Claims, No Drawings

FOREIGN PATENT DOCUMENTS

| | | | |
|---|---|---|---|
| EP | 0 130 052 | 1/1985 | |
| EP | 0136596 | 1/1985 | |
| EP | 0 178 935 | 4/1986 | |
| EP | 0182299 | 5/1986 | |
| EP | 0199138 | 10/1986 | |
| EP | 0335755 | 10/1989 | |
| EP | 0410351 | 1/1991 | |
| EP | 0 338 755 | 6/1993 | |
| EP | 0 683 181 | 11/1995 | ........... C08F/16/32 |
| EP | 0 633 274 | 1/1997 | |
| EP | 0 633 257 | 4/1997 | |
| EP | 0 683 181 | 9/1997 | |
| EP | 0690680 | 9/1997 | |
| EP | 0 683 149 | 10/1999 | |
| EP | 0 976 706 | 2/2000 | ........... C07C/43/16 |
| EP | 0835270 | 6/2000 | |
| EP | 01 10 8596 | 11/2003 | |
| FR | 2305462 | 10/1976 | |
| GB | 1514700 | 6/1978 | |
| GB | 1528341 | 10/1978 | |
| GB | 1528342 | 10/1978 | |
| WO | WO94/21697 | 9/1994 | |
| WO | 9702300 A | 1/1997 | |
| WO | WO98/46657 | 10/1998 | |
| WO | WO 98/46658 | 10/1998 | |
| WO | 9948939 A | 9/1999 | |
| WO | WO 99 48939 | 9/1999 | ........... C08F/21/26 |
| WO | WO00/12574 | 9/2000 | |
| WO | WO0127194 | 4/2001 | |
| WO | WO 01 46107 | 6/2001 | ........... C07C/41/18 |

OTHER PUBLICATIONS

"Development of Vulcanizable Elastomers Suitable For Use In Contact With Liquid Oxygen" J. Macromol. Sci.—(Phys.), B1(4), 815–830, Dec. 1967.

Copy of European Search Report for EP 01 108598.

Copy of International Search Report for PCT/US99/03490.

S.V. Kartsov et al., "The role of the reactor surface in the liquid–phase oxidation of hexafluorpropylene," Institute of Chemical Physics, Academy of Sciences of the USSR, Moscow (Translated from Izvestiya Akadermii Nauk SSSR, Seriya Khimicheskaya, No. 10, pp. 2268–2272, Oct. 1978.

L. L. Knunyants et al., Isv. Nauk SSr, Ser. Khim. 1954(2), 834–6.

G. Marchionni et al., "Photochemical Fluorination of Per-fluoropolyether Functional Derivatives," J. Fluorine Chemistry, 47: 515–525, 1990.

Worm Opposition 1, dated Jul. 30, 2003.

Worm Preliminary Motion, dated Jul. 30, 2004.

Navamini Opoostion 1, datee Aug. 1, 2004.

Navamini Preliminary Motion, dated Apr. 23, 2004.

* cited by examiner

METHOD OF MAKING FLUOROVINYL ETHERS AND POLYMERS OBTAINABLE THEREFROM

The present invention relates to Fluorovinyl ethers, the process for preparing them and the polymers obtainable therefrom.

It is well known that perfluoroalkyl vinyl ethers are generally used as monomers for the olefin copolymerization, specifically copolymerization with tetrafluoroethylene, vinylidene fluoride, chlorotrifluoroethylene (CTFE), and/or hexafluoropropene. The introduction of small amounts of perfluoroalkyl vinyl ethers in plastomeric polymers implies a higher polymer processability and better hot mechanical properties. The introduction of high amounts of perfluorovinyl ethers in crosslinkable fluoropolymers implies elastomeric properties at low temperature of fluorinated rubbers.

The need was felt, in the fluorinated polymeric material field, to produce both plastomers having good properties at high temperatures, and elastomers having improved properties at low temperatures by using only one fluorovinyl ether.

Such properties at low temperatures can generally be expressed by the glass transition temperature Tg.

Furthermore the need was felt to have available amorphous or crystalline copolymers having a low content of C(O)F end groups. A lower content of C(O)F end groups leads to obtain polymers having a higher thermal stability. A lower Tg allows to have elastomeric polymers which can be used at lower temperatures and therefore to have available elastomers with a wider use range. To obtain the combination of the above mentioned properties, fluorovinyl ethers must have a high unitary capability to modify the base backbone properties, as well as high reactivity to be used as comonomers both in plastomeric and in elastomeric fluoropolymers. It was desirable to have available vinyl ethers obtainable by simple processes having a limited number of steps. Preferably it would be desirable to have available a continuous process for preparing said vinyl ethers.

To solve the above identified technical problem, fluorovinyl ethers having different structural properties, have been proposed in the prior art. However from the prior art, hereinafter described, various unsolved problems result evident in the perfluorovinyl ether synthesis and in the preparation of the corresponding polymers having the combination of the above mentioned properties.

Patent U.S. Pat. No. 3,132,123 describes the preparation of perfluoroalkyl vinyl ethers, of the corresponding homopolymers and copolymers with TFE. Homopolymers are obtained under extreme experimental conditions, by using polymerization pressures from 4,000 to 18,000 atm. The perfluoromethylvinylether (PMVE) homopolymer is an elastomer: the Tg is not reported.

The general formula of the described vinyl ethers is the following:

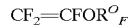

wherein $R^O_F$ is a perfluoroalkyl radical preferably from 1 to 5 carbon atoms. A process for preparing these vinyl ethers is described in Patent U.S. Pat. No. 3,291,843 wherein the starting acylfluoride is solidified and pyrolized with carbonates also in the presence of solvents. By this process undesired hydrogenated by products are obtained.

Patent U.S. Pat. No. 3,450,684 relates to vinyl ethers having the formula:

wherein $X^O$=F, Cl, $CF_3$, H and n' can range from 1 to 20. Also homopolymers obtained by UV polymerization are reported. The exemplified copolymers are not characterized by their properties at low temperatures.

Patent U.S. Pat. No. 3,635,926 relates to the emulsion copolymerization of perfluorovinyl ethers with TFE, showing that the presence of —C(O)F acylfluoride end groups makes the polymers unstable. The same phenomenon was already reported in U.S. Pat. No. 3,085,083 in the perfluorovinyl ether polymerization systems in solvent.

Patent U.S. Pat. No. 3,817,960 relates to the preparation and polymerization of perfluorovinyl ethers having the formula

wherein n" can range from 1 to 5. The compound synthesis is complex, it requires three steps. The preparation of the starting compound $CF_3O(CF_2O)_n.CF_2C(O)F$ is carried out by oxidation at low temperature in the presence of U.V. radiations; besides the condensation with HFPO (hexafluoropropenoxide) and the subsequent alkaline pyrolysis is necessary. No data on the above indicated properties are reported. With regard to this see Patent application U.S. Pat. No. 5,910,552.

Patent U.S. Pat. No. 3,896,179 relates to the separation of "primary" isomers of perfluorovinyl ethers, for example of $CF_3CF_2CF_2OCF=CF_2$ from the corresponding less stable "secondary" isomers $CF_3(CF_3)CFOCF=CF_2$. The latter are undesired products as regards both the polymer preparation and the poor properties of the obtained polymers.

Patent U.S. Pat. No. 4,340,750 relates to the preparation of perfluorovinyl ethers having the formula

wherein $R^O_f$ is a $C_1$–$C_{20}$ perfluoroalkyl optionally containing oxygen, $X^1$=H, Cl, Br, F, $COOR^O$, $CONR^OR'$ wherein $R^O$ is a $C_1$–$C_{10}$ alkyl group and R' represents H or a $C_1$–$C_{10}$ alkyl group. In the preparation of these compounds an acylfluoride together with iodine and tetrafluoroethylene is used, avoiding the final step of the acylfluoride pyrolysis which comes from the perfluoro-propene epoxide, by a deiodofluorination reaction, which takes place with low yields.

Patent U.S. Pat. No. 4,487,903 relates to the preparation of fluoroelastomeric copolymers (i.e., elastomeric fluoropolymers) using perfluorovinyl ethers having the formula:

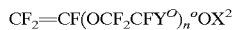

wherein $n^0$ ranges from 1 to 4; $Y^O$=F, Cl, $CF_3$, H; $X^2$ can be $C_1$–$C_3$ perfluoroalkyl group, $C_1$–$C_3$ ω-hydroperfluoroalkyl group, $C_1$–$C_3$ ω-chloroperfluoroalkyl group. The polymer has a content of fluorovinyl ether units ranging from 15 to 50% by moles. These vinyl ethers give copolymers which at low temperatures have better properties than those of the above mentioned perfluorovinyl ethers PVE (perfluoropropyl vinyl ether) and MVE type. In the patent it is disclosed that in order to have good properties at low temperature, the presence of at least two ether bonds in the side chain adjacent to the double bond is required. Furthermore from the patent it results that for values higher than 4 it is difficult to purify the monomers and the effect on the decrease of the polymer $T_g$ is lower. Besides the reactivity of the described vinyl ethers is very low and it is difficult to obtain polymers having a high molecular weight able to give good elastomeric properties. A TFE/perfluorovinyl ether copolymer (n°=2) 73/27% by moles with Tg of −32° C. is exemplified. However the polymer is obtained with very long reaction times (96 hours of polymerization).

Patent EP 130,052 describes the perfluoro(vinyl polyether) (PVPE) polymerization which leads to amorphous perfluoropolymers with a $T_g$ ranging from −15 to −100° C. The described polymers have $T_g$ values reaching up to −76° C.; the further $T_g$ decrease is obtained by using perfluoropolyethers as plasticizers. In the patent copolymers and terpolymers of TFE and MVE with vinylethers (PVPE) having the formula $$CF_2\!=\!CFO(CF_2CF(CF_3)O)_{n'''}\!-\!R^o{}_f$$

are described, wherein n''' ranges from 3 to 30 and $R^o{}_f$ is a perfluoroalkyl group. Due to purification difficulties, the used vinyl ethers are vinylether mixtures with different n''' values. According to said patent the most evident effect on the $T_g$ decrease is shown when n' is equal to or higher than 3, preferably higher than 4. According to the polymerization examples described in said patent the final mass of the polymer, besides the hot and under vacuum treatment, must then be washed with Freon® TF (chlorofluorocarbon) in order to remove all the unreacted monomer (PVPE). From the Examples it results that the reactivity of all the described monomers (PVPE) is poor.

U.S. Pat. No. 4,515,989 relates to the preparation of new intermediates for the fluorovinyl ether synthesis. According to the patent the vinylether synthesis is improved by using an intermediate able to more easily decarboxylate. For its preparation fluoroepoxides of formula:

$$X^3CF_2\!-\!CF\!-\!CF_2$$

wherein $X^3$=Cl, Br

are used.

U.S. Pat. No. 4,619,983 describes the copolymerization of VDF with vinyl ethers having the formula:

$$CF_2\!=\!CFOX^4$$

wherein $X^4$ is a $C_3$–$C_9$ oxyperfluoroalkyl radical containing from 1 to 3 oxygen atoms. The obtained polymers are not perfluorinated polymers and show a poor stability to alcohols.

U.S. Pat. No. 4,766,190 relates to the polymerization of perfluorovinylpolyethers (PVPE) similar to those of U.S. Pat. No. 4,487,903 with TFE and low perfluoropropene percentages, in order to improve the mechanical properties of the obtained polymers.

Patent EP 338,755 relates to the preparation of perfluorinated copolymers by using direct fluorination of partially fluorinated copolymers. More reactive partially fluorinated monomers are used, subjecting the obtained polymers are fluorinated with elemental fluorine. The fluorination step requires a supplementary process unit, besides in this step elemental fluorine is used, which is a highly oxidizing gas, with the consequent precautions connected to its use. Besides in the patent it is stated that in order not to compromise the fluorination reaction and the properties of the obtained polymer, using the invention process the percentage of the comonomer in the polymer cannot exceed 50% by moles.

U.S. Pat. No. 5,268,405 reports the preparation of perfluorinated rubbers having a low Tg, by the use of high viscosity perfluoropolyethers as plasticizers of perfluorinated rubbers (TFE/MVE copolymers). However during the use perfluoropolyether bleeds take place. This is true especially for the PFPE having a low molecular weight (low viscosity): in said patent, therefore, the high viscosity PFPE use is suggested, and therefore the low viscosity PFPEs must previously be removed from these last.

U.S. Pat. No. 5,350,497 relates to the preparation of perfluoroalkyl vinyl ethers by fluorination with elemental fluorine of hydrofluorochloroethers and subsequent dechlorination.

U.S. Pat. No. 5,401,818 relates to the preparation of perfluorovinyl ethers of formula:

$$R^1{}_f(OCF_2CF_2CF_2)_m, \!-\!OCF\!=\!CF_2$$

(wherein $R^1{}_f$ is a $C_1$–$C_3$ perfluoroalkyl radical and m, is an integer ranging from 1 to 4) and of the corresponding copolymers having improved properties at low temperature. The preparation of said perfluorovinyl ethers is carried out by 7 steps, some of them have very low yields, and comprise also a fluorination with elemental $F_2$. The reactivity of said perfluorovinyl ethers is anyhow low.

As it is shown from the above prior art, the perfluorovinyl ether synthesis generally involves a multistep process with low yields (U.S. Pat. Nos. 3,132,123 and 3,450,684), with additional purifications to remove undesired isomers (U.S. Pat. No. 3,896,179) and the need to control the undesired hydrogenated by-products (U.S. Pat. No. 3,291,843). Alternatively, in the synthesis substances acting as intermediates, which are suitably prepared, and which allow to eliminate said drawbacks (U.S. Pat. Nos. 4,340,750 and 4,515,989), are used.

Furthermore in some cases the vinylether preparation requires the fluorination with elemental fluorine of partially fluorinated intermediates (U.S. Pat. No. 5,350,497); or, to avoid synthesis and low reactivity problems of the perfluorovinyl ethers, fluorination of partially fluorinated polymers (EP 338,755) is suggested.

Other problems shown in the prior art relate to the low reactivity of the perfluorovinyl ethers, which makes it necessary the recovery of the unreacted monomers from the reaction raw products (English Patent UK 1,514,700), and the stability problems for the polymers having —C(O)F end groups (U.S. Pat. No. 3,635,926). These unstable end groups can be transformed by suitable reactants in order to increase the stability of the fluorinated polymer (EP 178,935).

Perfluoro(oxyalkyl vinyl ethers) are used to confer to the fluorinated rubbers good properties at low temperatures, and specifically to lower the copolymer glass transition temperature.

By increasing the perfluorooxyalkyl units forming the side perfluorooxyalkyl substituent, the $T_g$ of the corresponding obtainable amorphous copolymers decreases, but at the same time the reactivity of the vinylether drastically decreases, making more evident the previously shown problems for the recovery of the unreacted monomer from the raw polymerization products or from the polymer itself (U.S. Pat. No. 4,487,903—EP 130,052). In some cases, where the monomer cannot be completely removed by simple stripping under vacuum, more washings must then be carried out with fluorinated solvents to completely eliminate the unreacted vinyl ethers from the polymeric mass.

The perfluoromethylvinylether (MVE) is used as comonomer in plastomeric fluoropolymers and, at higher concentrations, also in elastomeric fluoropolymers. In particular, in EP 633,257 and EP 633,274 MVE is polymerized with TFE in the presence of small amounts of PVE or dioxoles to obtain polymers with improved flex life.

The amorphous copolymers of TFE with perfluoromethylvinylether have a $T_g$ around 0° C. or slightly lower (Maskornik, M. et al. "ECD-006 Fluoroelastomer—A High Performance Engineering Material". Soc. Plast Eng. Tech. Pao. (1974), 20, 675–7).

The extrapolated $T_g$ value of the MVE homopolymer is about −5° C. (J. Macromol. Sci.-Phys., B1(4), 815–830, Dec. 1967).

In U.S. Pat. Nos. 5,296,617 and 5,235,074 there is described the reaction of hypofluorite, $CF_2(OF)_2$, with unsaturated products, which contemporaneously leads to the formation of the dioxolane derivative and to the fluorinated olefin. Patent EP 683,181 describes the reactivity of $CF_2(OF)_2$ towards olefins, leading to the formation of linear reaction products between one hypofluorite molecule and two molecules of the same olefin, producing symmetric dienes.

The Applicant has surprisingly and unexpectedly found that it is possible to solve the above mentioned technical problems by using special fluoro vinyl ethers that are furthermore easily synthesized by a continuous process.

An object of the present invention is fluorovinyl ethers of general formula:

$$CFX=CXOCF_2OR \qquad (I)$$

wherein R is a $C_2$–$C_6$ linear, branched or $C_5$–$C_6$ cyclic (per)fluoroalkyl group, or a $C_2$–$C_6$ linear or branched (per)fluoro oxyalkyl group containing from one to three oxygen atoms. When R is a fluoroalkyl or fluorooxyalkyl group as above defined, it can contain 1 or 2 atoms, the same as or different from each other, selected from the following: H, Cl, Br, I; X=F, H. The term (per)fluoro refers to a molecule in which from one up to all of the hydrogens capable of being replaced with fluorine are replaced with fluorine.

The fluorovinyl ethers of general formula:

$$CFX=CXOCF_2OCF_2CF_2Y \qquad (II)$$

wherein Y=F, $OCF_3$ or X as above defined, are preferred among the compounds of formula (I).

The perfluorovinyl ethers of formula:

$$CF_2=CFOCF_2OCF_2CF_2Y \qquad (III)$$

wherein Y is as above defined, are particularly preferred. For example the perfluorovinyl ether of formula IV $$CF_2=CFOCF_2OCF_2CF_3 \qquad (IV)$$

can be mentioned as particularly preferred perfluorovinyl ethers.

Surprisingly, the vinyl ethers according to the invention show the advantages reported hereinafter with respect to the known vinyl ethers.

The advantages can be attributed to the —$OCF_2O$— unit directly bound to the ethylene unsaturation.

The Tg lowering obtained with the vinyl ethers of the invention is connected to the presence of the (—$OCF_2O$—) unit directly bound to the unsaturation. The Tg lowering is so surprisingly evident that it can be defined as a primary effect.

In fact, if the vinylether of the invention having two oxygen atoms is used:

$$CF_2=CF-O-CF_2-O-CF_2CF_3 \qquad (MOVE\ 1)$$

the Tg is clearly lower compared to the Tg of the polymer from PVE $$CF_2=CF-O-CF_2CF_2CF_3 \qquad (PVE)$$

and to the polymer from the vinyl ether having the same formula, but with the second oxygen atom in a different position and not having the characteristic unit (—$OCF_2O$—), i.e.

$$CF_2=CF-O-CF_2CF_2-O-CF_3 \qquad (PDE)$$

It is surprising to notice that with respect to MVE $$CF_2=CF-O-CF_3$$

the β-PDE vinyl ether does not give any advantage as regards Tg of the resulting polymers.

On the contrary, the primary effect of the (—$OCF_2O$—) unit is very clear in the polymers of the vinyl ethers of the present invention (MOVE).

It has surprisingly been found that the (—$OCF_2O$—) unit bound to the ethylene unsaturation of the vinyl ethers of the invention drastically increases the vinylether reactivity, reducing the rearrangements to C(O)F which cause instability in the resulting polymer.

The advantages of the present invention can be summarized as follows.

The reactivity of the new monomers allows preparation of copolymers having a high MW (molecular weight) with a very low content of carboxylic groups or derivatives thereof such as —C(O)F or —COO—. The carboxylic group content in the copolymer of a monomer of the present invention with TFE is about 10 times lower than that of a copolymer prepared under the same conditions but using perfluoropropyl vinyl ether (PVE) instead of the inventive fluorovinyl ethers of the present invention (see the Examples). As noted, a lower content of carboxylic groups, or of the corresponding derivatives (amides, esters, etc.) results in more stable polymers.

The reactivity of the monomers of the present invention is surprisingly high (see the homopolymerization Examples). The fluorovinyl ethers of the invention can be used as comonomers both in plastomeric (per)fluoropolymers (containing crystalline domains) and in elastomeric (per)fluoropolymers. To obtain plastomeric polymers the amount of the vinylether of the invention must be such to allow and lead to the formation of crystalline domains, generally <10% by moles. The presence of crystalline domains can be determined by DSC. To obtain amorphous polymers the amount of the vinylether of the invention must be such to lead to the disappearance of the crystalline domains. The skilled man in the art can easily find the amount of the vinylether of the invention which is required for obtaining said results.

The novel fluorovinyl ethers of the present invention can be used in amounts as low as about 0.1% on a mole basis. Generally the amount of the vinyl ether for obtaining amorphous polymers is higher than 10% by moles (i.e. 10 mole %), preferably in the range from about 15 to 20% by moles, or higher. In the case of copolymers having a high content of vinyl ether monomer, the low temperature properties (e.g. $T_g$) of the polymers of the invention are clearly better compared to copolymers having the same MVE content (see the Examples) and also, surprisingly, compared to copolymers where the perfluorovinyl ether of equal number of oxygen atoms does not have a —$OCF_2O$ group directly bound to the unsaturation, as in the case of the $CF_2=CFOCF_2CF_2OCF_3$ (β-PDE) (see the Examples).

The use of the monomers of the present invention in the polymerization reactions with fluoroolefins allows substantial and contemporaneous improvements over two important disadvantages of the prior art: the recovery of the unreacted vinylether and the polymer instability due to the presence of carboxylic end groups. A further advantage of the fluorovinyl ethers of the invention, as hereinafter illustrated, is that their preparation is carried out on a continuous basis by a limited number of steps. Furthermore, the raw materials used are inexpensive. The following raw materials can for example be mentioned $CF_2(OF)_2$, $CF_2=CF_2$, $CF_2=CFOCF_3$, $CHCl=CFCl$, $CFCl=CFCl$, $CF_2=CFCl$, $CF_2=CFH$, $CF_2=CH_2$, $CHCl=CHCl$ and other olefins. The use of these reactants is specified in the synthesis process of the vinyl ethers of the invention.

When used in connection with a quantity the term about refers to such normal variation in that quantity as would be expected by the skilled artisan.

As used herein, essentially free of crystalline zones or regions means that crystallinity is not detected by, for example, DSC, under typical ordinary conditions as would be used by the skilled artisan in routine experiments.

Polymers, homopolymers and copolymers are obtainable by polymerizing the fluorovinyl ethers of general formula (I)–(IV) alone or with at least one other monomer.

By copolymer, a polymer containing units derived from the vinyl ether of the invention and one or more comonomers, is meant.

Preferred comonomers are fluorinated compounds having at least one polymerizable double bond, $C=C$, optionally containing hydrogen and/or chlorine and/or bromine and/or iodine and/or oxygen.

Other comonomers that can be copolymerized with the fluorovinyl ethers of the present invention are non fluorinated $C_2$–$C_8$ olefins, i.e. olefinically unsaturated hydrocarbons such as ethylene, propylene, and isobutylene.

Among the usable comonomers the following can be mentioned:

$C_2$–$C_8$ perfluoroolefins, such as tetrafluoroethylene (TFE), hexafluoropropene (HFP), hexafluoroisobutene;

$C_2$–$C_8$ hydrogenated fluoroolefins, such as vinyl fluoride (VF), vinylidene fluoride (VDF), trifluoroethylene, $CH_2=CH$—$R^2_f$ perfluoroalkylethylenes, wherein $R^2_f$ is a $C_1$–$C_6$ perfluoroalkyl group;

$C_2$–$C_8$ chloro- and/or bromo- and/or iodo-fluoroolefins, such as chlorotrifluoroethylene (CTFE) and bromotrifluoroethylene;

$CF_2=CFOR^2_f$ (per)fluoroalkyl vinyl ethers (PAVE), wherein $R^2_f$ is a $C_1$–$C_6$ (per)fluoroalkyl group, for example a trifluoromethyl, bromodifluoromethyl or a heptafluoropropyl group;

$CF_2=CFOX^a$ (per)fluoro-oxyalkylvinyl ethers, wherein $X^a$ is: a $C_1$–$C_{12}$ alkyl, or a $C_1$–$C_{12}$ oxyalkyl group, or a $C_1$–$C_{12}$ (per)fluorooxyalkyl group having one or more ether groups, for example perfluoro-2-propoxypropyl.

sulphonic monomers having the structure $CF_2=CFOX^bSO_2F$, wherein $X^b=CF_2CF_2$, $CF_2CF_2CF_2$, $CF_2CF(CF_2X^c)$ wherein $X^c=F$, Cl, Br.

The process for preparing fluorinated polymers according to the present invention can be carried out by polymerization in organic solvent as described in U.S. Pat. Nos. 4,864,006 and 5,182,342, herein incorporated by reference. The organic solvent is selected from the group including chlorofluorocarbons, perfluoropolyethers, hydrofluorocarbons and hydrofluoroethers.

The process for preparing the polymers of the present invention can also be carried out by polymerization in aqueous emulsion according to well known methods in the art, in the presence of a radical initiator which can be selected from, for example: inorganic peroxides (for example alkaline metal or ammonium persulphates, perphosphates, perborates or percarbonates), optionally in combination with ferrous, cuprous or silver salts, or of other easily oxidizable metals; organic peroxides (for example, disuccinylperoxide, terbutylhydroperoxide, diterbutylperoxide); azocompounds (see U.S. Pat. Nos. 2,515,628 and 2,520,338, herein incorporated by reference). It is also possible to use organic or inorganic redox systems, such as ammonium persulphate/sodium sulphite or, hydrogen peroxide/aminoiminomethansulphinic acid to mentioned just a few.

Surfactants of various types are usually present in the reaction medium, among which the fluorinated surfactants of formula:

wherein $R^3_f$ is a $C_5$–$C_{16}$ (per)fluoroalkyl chain or a (per)fluoropolyoxyalkyl chain, $X^-$ is —COO$^-$ or —SO$_3^-$, $M^+$ is selected from $H^+$, $NH_4^+$, and an alkali metal ion are particularly preferred. Among the most commonly used surfactants, ammonium perfluorooctanoate, (per)fluoropolyoxyalkylenes terminated with one or more carboxylic groups, etc. can be mentioned.

During the polymerization, known iodinated a brominated chain transfer agents can be added to the reaction medium. It is also possible to use as chain transfer agents alkaline or alkaline earth metal iodides or bromides, according to U.S. Pat. No. 5,173,553, herein incorporated by reference.

Other chain transfer agents are mentioned in U.S. Pat. No. 4,766,190, herein incorporated by reference.

Crosslinking of the amorphous polymers of the present invention can be carried out according to methods well known in the art. When, for example, one of the comonomers is vinylidene fluoride or vinyl fluoride, curing can be carried out with polyamines or aromatic polyols in the presence of suitable catalysts (accelerants) as described in U.S. Pat. Nos. 3,876,654 and 4,259,463. When the monomer is perfluorinated, one generally uses in the copolymerization, in amounts lower than or equal to 3%, a comonomer having a reactive site that includes, for example, Br, I, CN, $OC_6F_5$, $COOR^a$ (wherein $R^a$ is an alkyl from 1 to 5 carbon atoms), or double bonds as described in U.S. Pat. No. 5,268,405. When the polymer contains Br or I, it is cured in the presence of a peroxide or a polyunsaturated compound as described in U.S. Pat. Nos. 4,948,852, 4,948,853 and 4,983,60, and EP 683,149.

Another object of the present invention is the synthesis process of the new (per)fluorovinyl ethers, which comprises the reaction of hypofluorite $CF_2(OF)_2$ with fluorinated olefin of formula $R_1R_2C=CR_3R_4$ to give a first intermediate hypofluorite F—$CR_1R_2$—$CR_3R_4$—$OCF_2OF$, the subsequent reaction of said compound with a second fluorinated olefin of formula $R_5R_6C=CR_7R_8$ to give second intermediate F—$CR_1R_2$—$CR_3R_4$—$OCF_2O$—$CR_5R_6$—$CR_7R_8$—F, which is converted by an elimination reaction such as dehalogenation or dehydrohalogenation to the novel perfluorovinyl ethers.

The general scheme of the synthesis is as follows:

a) $CF_2(OF)_2 + R_1R_2C=CR_3R_4 \rightarrow$ F—$CR_1R_2$—$CR_3R_4$—$OCF_2OF$ (VI)

b) F—$CR_1R_2$—$CR_3R_4$—$OCF_2OF + R_5R_6C^2=C^1R_7R_8$ - - - $\rightarrow$ F—$CR_1R_2$—$CR_3R_4$—$OCF_2O$—$C^2R_5R_6$—$C^1R_7R_8$—F (VII) dehalogenation./ c) F—$CR_1R_2$—$CR_3R_4$—$OCF_2O$—$C^2R_5R_6$—$C^1R_7R_8$—F - - - $\rightarrow$, /dehydrohalogenation. $CFX=CXOCF_2OR$ (I)

In this synthesis scheme, with reference to the formula of the compound (VII), $R_1$, $R_4$, are the same or different and are H, F; $R_2$, $R_3$; are the same or different and are H or Cl subject to the following conditions; (1) when the final reaction is to be a dehalogenation, $R_2=R_3=Cl$; (2) when the final reaction is to be a dehydrohalogenation one of the two substituents $R_2$ or $R_3$ is H and the other is Cl. Further $R_5$, $R_6$, $R_7$, $R_8$ are: F, or one of them is a $C_1$–$C_4$ linear or branched perfluoroalkyl group or a $C_1$–$C_4$ linear or branched perfluorooxyalkyl group containing from one to three oxygen atoms, or $R_5$ and $R_7$ or $R_6$ and $R_8$ are linked to each other to form with $C^2$ and $C^1$ a $C_5$–$C_6$ cyclic perfluoroalkyl group. Also, when one of the $R_5$ to $R_8$ radicals is a $C_2$–$C_4$ linear or branched fluoroalkyl or a $C_2$–$C_4$ linear or branched fluorooxyalkyl group containing from one to three oxygen atoms, one or two of the other $R_5$ to $R_8$ are F and one or two of the remainders, which can be the same as or different from each other, are selected from H, Cl, Br and; when two substituents are selected from H, Cl, Br or I, they are both linked to the same carbon atom. When $R_5$ and $R_7$ or $R_6$ and $R_8$ are linked each other to form with $C^2$ and $C^1$ a $C_5$–$C_6$ cycle fluoroalkyl group, one of the two free substituents $R_6$, $R_8$ or $R_5$, or $R_7$ is F and the other is selected from H, Cl, Br, Iodine.

The fluoroalkene used in reaction a) is replaceable with that of the subsequent reaction b). In this case the meanings defined for the substituents of the $R_1$–$R_4$ group, and respectively of the $R_5$–$R_8$ group, are interchangeable each other, with the proviso that the position of each radical of each of the two groups $R_1$–$R_4$ and $R_5$–$R_8$ with respect to —$OCF_2O$—on the chain of the intermediate compound (VII), is the same as would be if the synthesis takes place according to the above reported scheme and the two olefins each react in the considered steps.

In the first reaction a) of the above illustrated scheme, a hypofluorite gas flow $CF_2(OF)_2$, optionally suitably diluted with an inert fluid, comes into contact (i.e. is contacted with), in a suitable reactor with outlet, on the bottom of the same (first reactor), with the $R_1R_2C=CR_3R_4$ olefin, optionally diluted in an inert fluid and preferably in gas flow, to allow the chemical reaction a) with formation of the intermediate hypofluorite (VI). To maintain the reaction stoichiometry, the reactants must be introduced into the reactor in an approximately unitary molar ratio, or with an excess of $CF_2(OF)_2$. The residence time of the mixture in the reactor can range from about a few hundredths of second (e.g. about 0.05 seconds) up to about 120 seconds depending on the olefin reactivity, the reaction temperature, and the presence of optional reaction solvents.

The reaction temperature can range from about –40° to about –150° C., preferably from about –80° to about –130° C.

The compound (VI) usually is not separated from the reaction product and it is transferred in a continuous way to the subsequent reaction described in step b).

The mixture of the products coming out from the first reactor can be heated to room temperature before being fed into the second reactor.

In the second reaction b), the second olefin $R_5R_6C=CR_7R_8$, pure or in solution, reacts with the product obtained in the first reaction with formation of compound (VII).

The olefin can be fed in a continuous way, so as to maintain its concentration constant in the reactor; except for that normal variation as would be expected by the skilled artisan. The temperature of the reaction b) can range from about –20° to about –130° C., preferably from about –50° to about –100° C. The olefin concentration is higher than or equal to about 0.01M, preferably the concentration is higher than 3M, more preferably the olefin in a highly purified state is used.

The solvents useful in steps a) and b) are perfluorinated or chlorohydrofluorinated solvents or hydrofluorocarbons. Examples of said solvents are: $CF_2Cl_2$, $CFCl_3$, $CF_3CFH_2$, $CF_3CF_2CF_3$, $CF_3CCl_2H$, $CF_3CF_2Cl$.

In reaction c), the compound (VII), after distillation from the reaction product, is subjected to dechlorination or to dehydrochlorination as the case may be to obtain the vinyl ethers of formula (I). This last step can be carried out by using reactions widely described in the prior art. The suitable selection of the substituents $R_1$ to $R_8$ in the two olefins used in the synthesis allows one to obtain the vinyl ethers of the present invention.

Another object of the invention is a process wherein a hypofluorite of formula $X_1X_2C(OF)_2$, wherein $X_1$ and $X_2$ are the same or different and are F or $CF_3$, and two fluoroalkenes of formulas, respectively, $R^A_1R^A_2C=CR^A_3R^A_4$ and $R^A_5R^A_6C=CR^A_7R^A_8$, wherein $R^A_1$–$R^A_8$ are the same or different and are F, H, Cl, Br, I, —$CF_2OSO_2F$, —$SO_2F$, —$C(O)F$, $C_1$–$C_5$ linear or branched perfluoroalkyl or oxyperfluoroalkyl group, are reacted according to steps a) and b), excluding the dehalogenation or dehydrohalogenation step, to obtain compounds of general formula (VIII)

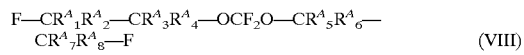

(VIII)

The following Examples are reported to illustrate the invention and they do not limit the scope of the same.

In the Examples the thermogravimetric analysis (TGA) is carried out at a heating rate of 10° C./min.

EXAMPLE 1

Synthesis of $CF_3CF_2OCF_2OCFClCF_2Cl$ perfluoro-1-2,dichloro-3,5-dioxaheptane

The reactor used is of the cylindrical type, with a total volume of about 300 ml and is equipped with magnetic dragging mechanical stirrer, turbine with recycle of the reacting gas placed at 20 cm from the reactor top, internal thermocouple, two internal copper pipes for the reactant feeding which end at about 1 mm from the turbine, and product outlet from the bottom. In the reactor, the internal temperature of which is maintained at –114° C., 1.1 l/h (liters/hour) of $CF_2(OF)_2$ and 3.3 l/h of He are introduced through one of the two inlet pipes. A flow of 1.1 l/h of $CF_2=CF_2$ and 0.7 l/h of He is maintained through the second inlet pipe. Feeding is continued for 6.6 hours.

The residence time of the transport gas in the reaction zone, comprised of the space between the outlet of the two feeding pipes in the reactor and the inlet of the discharge pipe, is of about 4 sec.

From the reactor bottom the reaction products are brought to room temperature and the flow of gaseous mixture, monitored by gas chromatography, is fed in a continuous way, under mechanical stirring, into a second reactor having a 250 ml volume maintained at the temperature of –70° C. and equipped with mechanical stirrer, thermocouple, dipping inlet for the reacting mixture, outlet with head of inert gas. The reactor contains 72.6 g of dichlorodifluoroethylene $CFCl=CFCl$.

At the end of the addition of reacting gases into the second reactor, the reaction raw material is distilled by a plate column at atmospheric pressure, collecting 41.5 g of the desired product (boiling point 91° C.).

The yield of perfluoro-1,2 dichloro-3,5-dioxaheptane, calculated with respect to $CF_2(OF)_2$, is 36%.

Characterization of perfluoro 1,2, dichloro-3,5-dioxaheptane

Boiling point at atmospheric pressure: 91° C.

$^{19}$F-NMR spectrum in p.p.m. (with respect to $CFCl_3$ at 0): −51.3/−53.0 (2F, O—$CF_2$—O); −70.6/−72.6 (2F, C—$CF_2Cl$); −78.0/−78.4 (1F, O—CFCl—C); −87.8 (3F, $CF_3$—C); −90.2/−91.8 (2F, C—$CF_2$—O).

Mass spectrum (E.I. electronic impact), main peaks and respective intensities: 69 (48.6%); 119 (84.3%); 151 (76.8%); 153 (69.8%); 185 (100%).

IR spectrum ($cm^{-1}$) intensity: (w)=weak, (m)=medium, (s)=strong, (vs)=very strong: 1407.3 (w); 1235.8 (vs); 1177.7 (vs); 1097.5 (vs); 1032.2 (s); 929.3 (w); 847.9 (m).

EXAMPLE 2

Synthesis of $CF_3OCF_2CF_2OCF_2OCFClCF_2Cl$ perfluoro-1,2-dichloro-3,5,8-trioxanonane (isomer A) and of $CF_3OCF(CF_3)OCF_2OCFClCF_2Cl$ perfluoro-1,2-dichloro-3,5,7-trioxa-6-methyloctane (Isomer B)

In a reactor identical to that used in Example 1, maintained at the same temperature of −114° C., 1.55 l/h of $CF_2(OF)_2$ and 4.5 l/h of He are introduced through one of the two inlet pipes; through the second inlet pipe 1.4 l/h of $CF_2$=CF—$OCF_3$ and 0.7 l/h of He are fed for 4.5 hours.

The residence time of the transport gas in the reaction zone comprised between the reactor outlet and the end of the two feeding pipes is of about 3 sec.

On the reactor bottom the reaction products are brought to room temperature and the gaseous mixture flow, monitored by gas chromatography, is fed in a continuous way, under mechanical stirring, into a second reactor identical to the one used for the same step in Example 1. Inside, where a temperature of −70° C. is maintained, there are 51 g of dichlorofluoroethylene CFCl=CFCl.

At the end of the addition of the reacting gases into the second reactor, the reaction raw material is distilled by a plate column at the reduced pressure of 250 mmHg. 50 g of a mixture formed by two isomers, respectively, isomer A) perfluoro-1,2-dichloro-3,5,8-trioxanonane and isomer 3) perfluoro-1,2-dichloro-3,5,7-trioxa-6-methyloctane are collected.

The mixture composition is determined by gas chromatography and is as follows: isomer A 79%, isomer B 21%. The molar yield of A+B with respect to the $CF_2(OF)_2$ used is 38%. The molar yield of A+B with respect to the used perfluoromethylvinylether is 42%. The isomers have been separated by preparative gas chromatography.

Characterization of Products A and B

Mixture boiling point (A 79%, B 21%) at the reduced pressure of 250 mmHg: 82° C.

$^{19}$F-NMR spectrum in p.p.m. (with respect to $CFCl_3$ at 0) of the isomer A: −50.6/−52.4 (2F, O—$CF_2$—O); −70.0/−71.8 (2F, C—$CF_2Cl$); −77.7 (1F, O—CFCl—C); −55.3/−55.6 (3F, $CF_3$—OC); −90.7/−91.1 (2F, C—$OCF_2$—C); −90.2/−90.6 (2F, C—OC—$CF_2OCOC$).

$^{19}$F-NMR spectrum in p.p.m. (with respect to $CFCl_3$ at 0) of isomer B: −50.0/−52.1 (2F, O—$CF_2$—O) −70.0/−71.8 (2F, C—$CF_2Cl$); −77.9 (1F, O—CFCl—C); −54.6/−54.9 (3F, $CF_3OC$); −85.7/−86.1 (3F, OC ($CF_3$)O); −100.3/−101.0 (1F, OCF(C)O).

Mass spectrum (electronic impact) main peaks and respective intensities:

Product A: 69 (50); 119 (100); 151 (50); 185 (42); 251 (38);

Product B: 69 (96); 97 (50); 135 (42); 151 (92); 185 (100).

IR spectrum ($cm^{-1}$), intensity of the mixture A 79%, B 21% ((w)=weak, (m)=medium, (s)=strong, (vs)=very strong): 1388 (w); 1288 (vs); 1233 (vs); 1151 (vs); 1104 (vs); 1032 (s); 846 (m); 685 (w)

EXAMPLE 3

Synthesis of $CF_3OCF_2CF_2OCF_2OCHClCHFCl$ perfluoro-1,2-dichloro-1,2-dihydro-3,5,8-trioxanonane (isomer C) and $CF_3OCF(CF_3)OCF_2OCHClCHFCl$ perfluoro-1,2-dichloro-1,2-dihydro-3,5,7-trioxa-6-methyloctane (Isomer D)

In a reactor identical to that used in Example 1, maintained at the temperature of −112° C., 1.55 l/h of $CF_2(OF)_2$ and 4.5 l/h of He are introduced through one of the two inlet pipes. Through the second inlet pipe 1.4 l/h of $CF_2$=CF—$OCF_3$ and 0.7 l/h of He are introduced for 5 hours.

The residence time of the transport gas in the reaction zone comprised between the reactor outlet and the end of the two feeding pipes is about 3 sec.

From the reactor bottom the reaction products are brought to room temperature and the gaseous mixture flow, monitored by gas chromatography, is fed in a continuous way, under mechanical stirring, into a second reactor identical to the one used for the same step in Example 1. Inside the second reactor the temperature is −70° C. and there are 50 g of 1,2-dichloroethylene CClH=CClH and 50 g of $CFCl_3$.

At the end of the addition of the reacting gases into the second reactor, after distillation of the solvent at room pressure, the reaction raw material is distilled through a plate column at the reduced pressure of 100 mmHg. 43.5 g of the mixture of the desired products (isomer C 78%, isomer D 22%, determined by gas chromatography) are collected. The molar yield of C+D with respect to the used $CF_2(OF)_2$ is 33%. The isomers have been separated by preparative gas chromatography.

Characterization of Products C and D

Mixture boiling point (78%, D 22%) at the reduced pressure of 100 mmHg: 71° C.

$^{19}$F-NMR spectrum in p.p.m. (with respect to $CFCl_3$ at 0) of the isomer C perfluoro-1,2-dichloro-1,2-dihydro-3,5,8-trioxanonane: −56. 0/−57.2 (2F, O—$CF_2$—O); −143.2/−146.0 (1F, C—CHFCl); −55.8 (3F, $CF_3$—OC); −91.0/−91.4 (2F, C—$OCF_2$—C); −90.3/−90.5 (2F, C—OC—$CF_2OCOC$).

$^{19}$F-NMR spectrum in p.p.m. (with respect to $CFCl_3$ at 0) of the isomer D perfluoro-1,2-dichloro-1,2-dihydro-3,5,7-trioxa-6-methyloctane: −56.0/−57.2 (2F, O—$CF_2$—O); −143.2/−146.0 (1F, C—CHFCl); −54.9/−55.1 (3F, $CF_3$—OC); −86.2/−86.3 (3F, OC($CF_3$)O); −100.5/−101.0 (1F, OCF(C)O).

$^1$H spectrum in p.p.m. (with respect to TMS) of the isomers C and D: 6.28/6.05 (1H —CHFCl); 6.02/5.95 (1H —CHCl—)

Mass spectrum (electronic impact), main peaks and respective intensities %: 69 (84); 119 (100); 185 (51.1); 251 (84); 281 (15.8); 283 (4.8); 347 (5.7); 349 (1.7).

IR spectrum ($cm^{-1}$) intensity ((w)=weak, (m)=medium, (s)=strong, (vs)=very strong): 3001.0 (w); 2920.9 (w); 2850.9 (w); 1286.3 (vs); 1233.7 (vs); 1125.5 (vs); 1081.8 (s); 1047.9 (s); 815.9 (m); 766.3 (m).

EXAMPLE 4

Dehalogenation of perfluoro 1,2-dichloro-3,5-dioxaheptane

In a 25 ml three-necked flask, equipped with mechanical stirrer, thermometer, dropping funnel, distillation column equipped with water refrigerant and collecting trap maintained at −78° C. and connected to a mechanical vacuum pump, 150 ml of DMF, 15 g of powdered Zn, 0.5 g of $K_2CO_3$, and 100 mg of $I_2$ are introduced. The internal temperature is brought to 80° C. and 50 g of perfluoro-1,2-dichloro-3,5-dioxaheptane are added dropwise. When the addition is over, the mixture is allowed to react for about 30 minutes. At the end, the internal pressure is gradually brought from 760 mmHg to 300 mmHg. After about 20 minutes, the collecting trap containing 34.2 g of perfluoro-3,5-dioxa-1-heptene (MOVE 1) is disconnected.

The dehalogenation yield is 85%.

Characterization of perfluoro-3,5-dioxa-1-heptene (MOVE 1)

Boiling point at atmospheric pressure: 41.9° C.

$^{19}$F-NMR spectrum in p.p.m. with respect to $CFCl_3$ at 0: −56.8 (2F, O—$CF_2$—O); −87.2 (3F, $CF_3$—C); −90.6 (2F, C—$CF_2$—O); −114 (1F, O—C=C—F) −121.8 (1F, O—C=CF); −137 (1F, O—C—F=C);

Mass spectrum (electronic impact), main peaks and respective intensities: 69 (66.5%); 119 (100%); 147 (83.4%); 185 (89.4%); 216 (67.3%); 282 (8.2%).

IR spectrum ($cm^{-1}$) intensity ((w)=weak, (m)=medium, (s)=strong, (vs)=very strong: 1839.5 (m); 1407.6 (w); 1307.4 (vs); 1245.8 (vs); 1117.4 (vs); 907.2 (m); 846.0 (m).

EXAMPLE 5

Dehalogenation of the Isomer Mixture A+B Obtained in Example 2 (perfluoro-1,2-dichloro-3,5,8-trioxanonane $CF_3OCF_2CF_2CF_2OCFClCF_2Cl$+ perfluoro-1,2-dichloro-3,5,7-trioxa-6-methyloctane $CF_2OCF(CF_3)OCF_2OCFClCF_2Cl$).

In a 250 ml flask equipped as described in the previous Example 4, 110 ml of DMF, 10 g of Zn in powder and 0.3 ml of $Br_2$ are introduced. The internal temperature is brought to 75° C. and 30.3 g of the binary mixture A+B separated in the previous Example 2 are added dropwise. When the addition is over, the mixture is allowed to react for about 3 hours. At the end, the internal pressure is gradually lowered from 760 mmHg to 200 mmHg at −79° C. After about 30 minutes the collecting trap is disconnected. The trap contents, which are washed with water, are recovered. Twenty-four grams of a mixture formed of 79% (gas chromatographic determination) perfluoro-3,5,8-trioxa-1-nonene (MOVE '2) $CF_3OCF_2CF_2OCF_2OCF=CF_2$ (isomer A'), and 21% perfluoro-3,5,7-trioxa-6,methyl-1 octene (MOVE 2a) $CF_3OCF(CF_3)OCF_2O—CF=CF_2$ (isomer B') are obtained. The mixture is then separated by preparative gas chromatography.

Characterization of Products A' and B'

Boiling range of the isomer mixture at atmospheric pressure: 72.5°–74.5° C.

$^{19}$F-NMR spectrum in p.p.m. (with respect to $CFCl_3$ at 0) of the isomer A': −55.9 (3F, $CF_3$—O); −56.9 (2F, O—$CF_2$—O); −90.8 (2F, C—$CF_2$—O); −91.2 (2F, O—$CF_2$—C); −114 (1F, O—C=C—F); −121.8 (1F, —O—C=CF); −137 (1F, O—CF=C)

$^{19}$F-NMR spectrum in p.p.m. (with respect to $CFCl_3$ at 0) of the isomer B': −55.9 (3F, $CF_3$—O); −56.2 (2F, O—$CF_2$—O); −86.4 (3F, $CF_3$—C); −100.9 (1F, CF; −114 (1F, O—C=C—F); −122 (1F, O—C=CF); −137 (1F, O—CF=C).

Mass spectrum (electronic impact), main peaks and respective intensities of the isomer A': 69 (74); 81 (18); 119 (100); 147 (59); 185 (26); 251 (21);

Mass spectrum (electronic impact), main peaks and respective intensities of the isomer B': 69 (80); 81 (37); 97 (47); 119 (36); 147 (100); 185 (19).

IR spectrum ($cm^{-1}$) intensity ((w)=weak, (m)=medium, (s)=strong, (vs)=very strong): 1839 (m); 1343 (s); 1248 (vs); 1145 (vs); 918 (m); 889 (m).

EXAMPLE 6

Dehalogenation of the Isomers C+D Mixture Obtained in Example 3 ($CF_3OCF_2CF_2OCF_2OCHClCHFCl$ perfluoro-1,2-dichloro-1,2-dihydro-3,5,8-trioxanonane (isomer C)+$CF_3OCF(CF_3)OCF_2OCHClCHFCl$ perfluoro-1,2-dichloro-1,2-dihydro-3,5,7-trioxa-6-methyloctane (Isomer D))

In a 500 ml three-necked flask, equipped with mechanical stirrer, thermometer, dropping funnel, distillation column having a water refrigerant and a collecting trap maintained at the temperature of −78° C., 250 ml of DMF, 30 g of zinc powder, and 300 mg of $I_2$ are introduced.

The temperature is brought to 100° C. and 56.9 g of the isomer mixture obtained in Example 3 are added dropwise.

When the addition is, over the reactor internal temperature is brought to 120° C. and stirring is maintained for 24 hours. At the end, the reaction product, which contains traces of solvent and which is collected in the trap maintained at −78° C., is distilled. After washing with water, 35 g of a mixture of perfluoro-1,2-dihydro-3-5-8-trioxa-1-nonene (isomer C', 79% by mole) and of perfluoro-1,2-dihydro-3-5-7-trioxa-5-methyl-1-octene (isomer-D', 21% by mole) is recovered. The isomers are separated by preparative gas chromatography.

The dehaloagenation reaction yield is 76%.

Characterization of Products C' and D'

Boiling range of the mixture of isomers C' 79%, D' 21% at atmospheric pressure: 90.0°–92.0° C.

$^{19}$F-NMR spectrum in p.p.m. (with respect to $CFCl_3$ at 0) of the isomer C' perfluoro-1,2-dihydro-3,5,8-trioxa-1-nonene: −55.7 (3F, $CF_3$—O) ; −57.3 (2F, O—$CF_2$—O); −90.9 (2F, C—$CF_2$—O); −91.2 (2F, O—$CF_2$—C) ; −149.3/−150.0 (1F, O—C=C—F).

$^{19}$F-NMR spectrum in p.p.m. (with respect to $CFCl_3$ at 0) of the isomer D' perfluoro-1,2-dihydro-3,5,7-trioxa-6-methyl-1-octene: −55.0 (3F, $CF_3$—O); −56.9 (2F, O—$CF_2$—O); −86.2 (3F, $CF_3$—C); −101.0 (1F, CF) −149.3/−150,0 (1F, O—C=C—F)

Mass spectrum (electronic impact), main peaks and respective intensities %: 69 (82); 119 (100); 185 (29); 246 (25); 251 (20); 312 (43).

IR spectrum ($cm^{-1}$) intensity of the isomer mixture (C' 79%, D' 21%) ((w)=weak, (m)=medium, (s)=strong, (vs)=very strong); 3140 (w); 1722 (w); 1695 (w); 1402 (m); 1281 (vs); 1237 (vs); 1147 (vs); 1106 (vs); 1030 (m).

EXAMPLE 7

Homopolymerization of perfluoro-3,5-dioxa-1-heptene (MOVE 1)

In a glass reactor for polymerization, having a 20 ml volume, equipped with magnetic stirrer and with an inlet for the reactant feeding and discharge, 60 µl of perfluoropropionylperoxide at 3% by weight in $CFCl_2CF_2Cl$ and 3 g of MOVE 1are sequentially introduced. The so-charged reactor is brought to the temperature of −196° C., evacuated, brought to room temperature. The cooling-evacuation procedure is repeated. At the end of the degassing operations the reactor is thermostated at the temperature of 30° C. and the mixture is allowed to react under these conditions for two days with magnetic stirring.

The reaction raw material which is finally recovered appears as a slightly viscous, transparent, colourless and homogeneous solution.

After distillation of the unreacted monomer and subsequent stripping under vacuum at 150° C. for 3 hours, 180 mg of the polymer are separated.

The IR analysis of the obtained polymer shows that, in the spectrum, absorption bands in the region of fluorinated double bonds are absent.

The $^{19}$F-NMR analysis carried out on the polymer dissolved in $C_6F_6$ is in accordance with the homopolymer structure having a molecular weight of 50,000. The analysis does not show the presence of unreacted monomer.

The DSC thermogram does not show any melting endothermic curve, wherefore the polymer is amorphous. The polymer $T_g$, determined by DSC, is −35.4° C. The thermogravimetric analysis (TGA) shows a weight loss of 2% at 332° C. and of 10% at 383° C.

EXAMPLE 8

Copolymer between perfluoro-3,5,8-trioxa-1-nonene $CF_3OCF_2CF_2OCF_2OCF=CF_2$ (MOVE 2) and perfluoro-3,5,7-trioxa-6,methyl-1-octene $CF_3OCF(CF_3)OCF_2O—CF=CF_2$ (MOVE 2a).

In a reactor having the same characteristics as that described in Example 7, 150 µl of perfluoropropionylperoxide at 3% by weight in $CFCl_2CF_2Cl$ and 3.2 g of a mixture prepared according to the process of Example 5 and containing 83% MOVE 2 and 17% MOVE 2a, are introduced. The reactor is then evacuated, cooled, and the subsequent reaction carried out as described in the previous Example 7.

The raw reaction product appears as a slightly viscous, transparent, colourless and homogeneous solution. The unreacted monomers are distilled and a stripping under vacuum at 150° C. for 3 hours is thereafter carried out. Finally, 350 mg of the polymer are separated.

The IR analysis shows that, in the polymer spectrum, absorption bands in the region of the fluorinated double bonds are absent.

The $^{19}$F-NMR analysis is in accordance with the copolymer structure having an average molecular weight of 35,000 and a MOVE 2/MOVE 2a content equal to the percentages of the respective monomers in the reacting mixture. Unreacted monomers are not evident.

The DSC thermogram does not show any melting endothermic curve, wherefore the polymer is amorphous. The polymer $T_g$, determined by DSC, is −52.6° C. The thermogravimetric analysis (TGA) shows a weight loss of 2% at 280° C. and of 10% at 327° C.

EXAMPLE 9

Crystalline Copolymer between MOVE 1 and TFE

A 5 l steel AISI 316 autoclave with stirrer operating at 650 rpm is used. After evacuation of the autoclave, 3 l of demineralized water, 15.70 g of MOVE 1 and the microemulsion prepared according to the procedure described in U.S. Pat. No. 4,864,006 are sequentially introduced, so as to have a concentration of 2 g of surfactant/l of water.

The autoclave is heated to 75° C. and then pressurized to 0.32 bar with ethane. A gaseous mixture in a molar ratio of 54.55 TFE/MOVE 1 is pumped by a compressor until internal pressure on the autoclave is 21 absolute bar.

The composition of the gaseous mixture present in the top of the autoclave is analyzed by gas chromatography.

Before the reaction is started, the gaseous phase has the following molar percentages of the reactants: 93.1% TFE, 5.5% MOVE 1 and 1.4% Ethane. The reaction is triggered by feeding, in a continuous way by a metering pump a 0.0031 molar potassium persulphate solution at a flow rate of 88 ml/h.

The pressure is maintained constant by feeding additional monomer mixture. The polymer synthesis is stopped after 742 g of mixture have been fed in total.

The reactor is cooled to room temperature, the emulsion is discharged, and coagulation is induced by addition of $HNO_3$ (65%).

The polymer is separated, washed with water and, dried at 220° C.

The IR analysis shows the presence of very small absorption bands in the carboxyl zone, the intensity of which is about half of that obtained for a TFE/PVE copolymer film having the same thickness, prepared according to the comparative Example 3. The MFI according to ASTMVD 1238-52T was 4.4. The polymer therefore is thermally more stable (see the comparative Example hereunder).

EXAMPLE 10

Amorphous Copolymer between MOVE 1 and TFE

In an AISI-316 polymerization reactor having a 40 ml volume, equipped with magnetic stirring, pressure transducer, and an inlet for the reactant feeding and discharge, 250 µl of perfluoropropionylperoxide at 3% by weight in $CFCl_2CF_2Cl$, 9.8 mmoles of MOVE 1, and 18 mmoles of tetrafluoroethylene are introduced.

The reactor is cooled to −196° C., evacuated, then brought to room temperature. The cooling-evacuation procedure is repeated twice.

At the end of the degassing operations, the reactor is thermostated at the temperature of 30° C. and the reaction mixture maintained under magnetic stirring. The internal pressure decreases from 6.4 atm to 4.7 atm in about 8 hours (reaction time).

After distillation of the unreacted monomers and polymer stripping under vacuum for 3 hours at 150° C., 1,100 mg of polymer are recovered. The polymer appears as a transparent and colourless rubber.

By $^{19}$F-NMR analysis of the polymer dissolved with heating in $C_6F_6$, it is determined that the MOVE 1 molar percentage in the polymer is 24%.

The IR analysis does not show, in the polymer spectrum, absorption bands in the region of the fluorinated double bonds and shows the presence of very small absorption bands in the region of the carboxyl bands. The intensity of these signals, compared to ones in the same region obtained from a film having the same thickness but made of polymer of the comparative Example 1, is equal to about ¹/₁₀ of the latter. p The DSC thermogram does not show any melting endotherm, wherefore the polymer is amorphous. The $T_g$ determined by DSC is −21.4° C.

The TGA shows a weight loss of 2% at 450° C. and of 10% at 477° C. The polymer therefore is thermally more stable (see the comparative Example hereunder) with respect to the comparative Example (see below).

The polymer intrinsic viscosity measured at 30° C. in Fluorinert® FC-75, is 35.5 ml/g.

EXAMPLE 11

Amorphous Copolymer between MOVE 1 and TFE

In an AISI-316 polymerization reactor identical to that described in the previous Example 10, 250 µl of perfluoropropionylperoxide at 3% by weight in $CFCl_2CF_2Cl$, 9.75 mmoles of MOVE 1 and 9 mmoles of tetrafluoroethylene are sequentially introduced.

The procedure already described in the previous Example 10 is followed until the thermostating step at the temperature of 30° C. under magnetic stirring. During the reaction the internal pressure decreases from 3.4 atm to 2.9 atm in about 8 hours.

At the end, the unreacted monomers are distilled and the polymer is stripped under vacuum at 150° C. for 3 hours.

480 mg of the polymer are separated.

By $^{19}$F-NMR analysis of the polymer dissolved with heating in $C_6F_6$, it is determined that the MOVE 1 molar percentage in the polymer is 39%.

The IR analysis shows that, in the polymer spectrum, absorption bands in the region of the fluorinated double bonds are absent.

The DSC thermogram does not show any melting endothermic curve, wherefore the polymer is amorphous. The $T_g$ determined by DSC is -29.8° C.

The TGA shows a weight loss of 10% at 435° C.

EXAMPLE 12

Amorphous Copolymer between MOVE 1 and $CF_2=CH_2$

In a polymerization reactor identical to that described in Example 10, 250 µl of perfluoropropionylperoxide at 3% by weight in $CFCl_2CF_2Cl$, 10 mmoles of MOVE 1, and 18 mmoles of VDF are sequentially introduced.

The procedure already described in the previous Example 10 is followed until the thermostating step at the temperature of 30° C. under magnetic stirring. The internal pressure decreases from 6.8 atm to 5.0 atm during the reaction (about 8 hours).

After distillation of the unreacted monomers and subsequent polymer stripping under vacuum at 150° C. for 3 hours, 1,600 mg of the polymer are separated, appearing as a transparent and colourless rubber.

By the $^{19}$F-NMR analysis carried out on the polymer dissolved in $C_6F_6$, it is determined that the MOVE 1 molar percentage in the polymer is 40%.

The DSC thermogram does not show any melting endothermic curve, wherefore the polymer is amorphous. The $T_g$ determined by DSC, is -47° C.

The TGA shows a weight loss of 2% at 428° C. and of 10% at 455° C.

EXAMPLE 13

Amorphous Terpolymer MOVE 2/MOVE 2a/TFE

In a polymerization reactor identical to that described in Example 10, 100 µl of perfluoropropionylperoxide at 6% by weight in $CFCl_2CF_2Cl$, 10 mmoles of a MOVE 2 (83%) and MOVE 2a (17%) mixture (synthesized according to the process of Example 5), and 18 mmoles of tetrafluoroethylene (TFE) are sequentially introduced.

The procedure already described in the previous Example 10 is then followed until thermostating at the temperature of 30° C. under magnetic stirring. The internal pressure decreases from 6.1 atm to 3.9 atm during the reaction (about 8 hours).

After distillation of the unreacted monomers and polymer stripping under vacuum at 150° C. for 3 hours, 1,131 mg of the polymer are separated.

By the $^{19}$F-NMR analysis carried out on the polymer dissolved in $C_6F_6$, the total molar percentage of the MOVE 2+MOVE 2a perfluorovinyl ethers units in the polymer is 22%; the MOVE 2/MOVE 2a ratio by moles in the polymer is 83/17 (equal to that of the starting feed mixture).

The presence of unreacted monomers is not evident.

The IR analysis does not show, in the polymer spectrum, absorption bands in the region of the fluorinated double bonds, and it shows the presence of very small absorption bands in the zone of the carboxyl signals. The intensity of these signals, compared with the similar ones obtained from a film having the same thickness obtained with the polymer of the comparative Example 1, is equal to about 1/10 of the latter.

The DSC thermogram does not show any melting endotherm, wherefore the polymer is amorphous. The $T_g$ determined by DSC, is -37.5° C.

The TGA shows a weight loss of 10% at 473° C.

The polymer intrinsic viscosity measured at 30° C. in Fluorinert® FC-75, is 40.0 ml/g.

EXAMPLE 14

Amorphous Terpolymer MOVE 2/MOVE 2a/TFE

In a polymerization reactor identical to that described in Example 10, 100 µl of perfluoropropionylperoxide at 6% by weight in $CFCl_2CF_2Cl$, 9.7 mmoles of the MOVE 2 (83%) and MOVE 2a (17%) mixture synthesized according to the process of Example 5, and 10 mmoles of tetrafluoroethylene (TFE) are sequentially introduced.

The procedure already described in the previous Example 10 is then followed until the thermostating step at the temperature of 30° C. under magnetic stirring. The internal pressure decreases from 3.6 atm to 2.7 atm during the course of reaction (about 8 hours).

After distillation of the unreacted monomers and polymer stripping under vacuum at 150° C. for 3 hours, 652 mg of polymer are separated.

By the $^{19}$F-NMR analysis carried out on the polymer dissolved in $C_6F_6$, the total molar percentage of units derived from the MOVE 2+MOVE 2a perfluorovinyl ethers in the polymer is 37%; the MOVE 2/MOVE 2a molar ratio in the polymer is 83/17 (equal to that of the starting feed mixture).

The presence of unreacted monomers is not evident.

The IR analysis does not show, in the polymer spectrum, absorption bands in the region of the fluorinated double bonds.

The DSC thermogram does not show any melting endothermic curve, wherefore the polymer is amorphous. The $T_g$ determined by DSC, is -44.5° C.

The TGA shows a weight loss of 10% at 451° C.

The polymer intrinsic viscosity measured at 30° C. in Fluorinert® FC-75, is 16.7 ml/g.

EXAMPLE 15

Amorphous Copolymer between perfluoro-1,2-dihydro-3,5,8-trioxa-1-nonene (H-MOVE 2) and perfluoro-1,2-dihydro-3,5,7-trioxa-6-methyl-1-octene (H-MOVE 2a) with Molar Ratio 88/12

In a reactor identical to that described in Example 7, 200 μl of perfluoropropionylperoxide at 3% by weight in $CFCl_2$—$CF_2Cl$ and 3.1 g of an 88/12 H-MOVE 2/H-MOVE 2a 88/12 mixture are introduced.

The procedure described in Example 7 is followed.

The recovered reaction raw material appears as a slightly viscous, transparent, colourless and homogeneous solution.

After distillation of the unreacted monomer and subsequent stripping under vacuum at 150° C. for 3 hours, 120 mg of polymer are separated.

The IR analysis of the polymer obtained shows that, in the polymer spectrum, absorption bands in the region of the fluorinated double bonds are absent.

The $^{19}$F-NMR analysis is in accordance with the copolymer structure having a content of monomers H-MOVE 2 and H-MOVE 2a equal to the H-MOVE 2 and H-MOVE 2a percentages in the reacting mixture. The analysis does not show the presence of unreacted monomers.

The DSC thermogram does not show any melting endotherm, wherefore the polymer is amorphous. The polymer $T_g$ determined by DSC, is -58.0° C. The thermogravimetric analysis (TGA) shows a weight loss of 10% at 307° C.

EXAMPLE 16

Terpolymer H-MOVE 2/H-MOVE 2a/TFE

In a reactor similar to that described in Example 10, 100 μl of perfluoropropionylperoxide at 6% by weight in $CFCl_2$—$CF_2Cl$, 5 mmoles of a H-MOVE 2 (88%) and H-MOVE 2a (12%) mixture, and 18 mmoles of tetrafluoroethylene are introduced.

The same procedure described in Example 10 is followed.

At the end of the degassing, the reactor is thermostated at the temperature of 30° C. under magnetic stirring. The internal pressure decreases from 6.8 atm to 6.5 atm in about 6 hours (reaction time). p After distillation of the unreacted monomers and polymer stripping under vacuum at 150° C. for 3 hours, 300 mg of the polymer are separated.

By $^{19}$F-NMR analysis of the polymer dissolved under heating in $C_6F_6$ it is calculated that the molar percentage (mole %) of units derived from the perfluorovinyl ethers (H-MOVE 2+H-MOVE 2a) contained in the polymer is 33%. The H-MOVE 2/H-MOVE 2a molar ratio in the polymer is equal to the H-MOVE 2/H-MOVE 2a molar ratio of the feed mixture. Unreacted monomers are not evident.

The IR analysis does not show, in the polymer spectrum, absorption bands in the zone of the fluorinated double bonds.

The DSC thermogram does not show any melting endotherm, wherefore the polymer is amorphous. The $T_g$ determined by DSC, is -44.5° C.

The TGA shows a weight loss of 10% at 450° C.

Example 1 (Comparative)

Copolymer PVE/TFE

In a polymerization reactor identical to that described in Example 10, 250 μl of perfluoropropionylperoxide at 3% by weight in $CFCl_2CF_2Cl$, 9.8 mmoles of PVE, and 18 mmoles of tetrafluoroethylene, are sequentially introduced.

The procedure already described in the previous Example 10 is followed until thermostating at the temperature of 30° C. under magnetic stirring. The reaction time is eight hours.

After distillation of the unreacted monomers and stripping under vacuum at 150° C. for 3 hours, 540 mg of the polymer are recovered.

By the $^{19}$F-NMR analysis carried out on the polymer dissolved in $C_6F_6$, it is calculated that the PVE molar percentage in the polymer is 23%.

The IR analysis shows that, in the polymer spectrum, there are absorption bands in the carboxyl zone, whose intensity is 10 times higher than that obtained from a film of a MOVE 1/TFE copolymer prepared according to Example 10 and having the same thickness.

The DSC thermogram does not show any melting endothermic curve, wherefore the polymer is amorphous. The TGA shows a weight loss of 2% at 427° C. and of 10% at 463° C. The $T_g$, determined by DSC, is +15° C.

The polymer intrinsic viscosity, measured at 300C in Fluorinert® FC-75, is 51 ml/g.

Example 2 (Comparative)

Copolymer between β-PDE ($CF_3OCF_2CF_2OCF$=$CF_2$)/TFE

In a polymerization reactor identical to that described in Example 10, 250 μl of perfluoropropionylperoxide at 3% by weight in $CFCl_2$—$CF_2Cl$, 10 mmoles of β-PDE, and 18 mmoles of tetrafluoroethylene, are in sequence introduced.

The procedure described in the previous Example 10 is followed until the thermostating step at the temperature of 30° C. under magnetic stirring.

By the $^{19}$F-NMR analysis carried out on the polymer purified of monomers by the processes described in the previous Examples, it is calculated that the molar percentage of β-PDE in the polymer is 23%.

The DSC thermogram does not show any melting endothermic curve wherefore the polymer is amorphous. The $T_g$, determined by DSC, is -4.8° C.

This Tg value is clearly higher than those obtainable with the vinyl ethers of the invention (see the above Examples).

Example 3 (Comparative)

Crystalline Copolymer PVE/TFE (PFA)

One operates as in Example 9 except that in this case the perfluoropropylvinyl ether (PVE) is used instead of α-PDE to obtain a copolymer having MFI equal to that of the Example copolymer of 9.

The IR analysis shows absorption bands in the carboxyl zone, the intensity is of which double those obtained for a TFE/MOVE 1 copolymer film of equal thickness and prepared according to Example 9.

What is claimed is:

1. A process for making fluorovinyl ether of formula

wherein:
1) R is a $C_2$–$C_6$ linear or branched perfluoroalkyl group, a $C_5$–$C_6$ cyclic perfluoroalkyl group, or a linear or branched perfluorooxyalkyl group comprising 2 or 6 carbon atoms and 1 to 3 oxygen atoms;

2) up to two fluorine atoms of the perfluoroalkyl group or the perfluorooxyalkyl group can be independently replaced with an atom selected from the group consisting of H, Cl, Br, and I; and 3) X is F or H; comprising the steps of a) contacting hypofluorite, $CF_2(OF)_2$, with a first olefin of structure $R_1R_2C=CR_3R_4$, wherein $R_1$ and $R_4$ are the same or different and selected from H and F, and $R_2$ and $R_3$ are the same or different and selected from H and Cl, to form a first intermediate hypofluorite of structure $$F-CR_1R_2-CR_3R_4-O-CF_2OF \qquad (VI)$$

and b) contacting the first intermediate hypofluorite (VI) with a second olefin having structure $R_5R_6C^2=C^1R_7R_8$ to form a second intermediate hypofluorite $$F-CR_1R_2-CR_3R_4-OCF_2O-C^2R_5R_6-C^1R_7R_8-F \qquad (VII)$$

wherein $R_5$, $R_6$, $R_7$, and $R_8$ are F; or one of $R_5$, $R_6$, $R_7$, and $R_8$ is a $C_1$–$C_4$ linear or branched perfluoroalkyl group and the others $R_5$, $R_6$, and $R_7$, and $R_8$ are F; or one of $R_5$, $R_6$, $R_7$, and $R_8$ is a $C_1$–$C_4$ linear or branched perfluorooxyalkyl group containing from one to three oxygen atoms and the others of $R_5$, $R_6$, $R_7$, and $R_8$ are F; or either pairing $R_5$ and $R_7$ or $R_6$ and $R_8$, together with the carbon atoms to which they are attached, are linked to form a perfluorinated $C_5$–$C_6$ cycloalkyl group and the others of $R_5$, $R_6$, $R_7$, and $R_8$ not so linked are F; and c) when $R_2$ and $R_3$ are both Cl, subjecting the second intermediate (VII) to a dehalogenation reaction, or, when one of $R_2$ and $R_3$ is H, subjecting the second intermediate (VII) to a dehydrohalogenation reaction;

with the proviso that when one of $R_5$, $R_6$, $R_7$ or $R_8$ is a $C_2$–$C_4$ linear or branched fluoroalky group or a $C_2$–$C_4$ linear or branched fluoroalkoxy group comprising from one to three oxygen atoms; then one or two of the remaining three of $R_5$, $R_6$, $R_7$, and $R_8$ are F and the remaining one or two of $R_5$, $R_6$, $R_7$, $R_8$ are selected from H, Cl, Br, and I, with the proviso that, where only one of said remaining three of $R_5$, $R_6$, $R_7$, and $R_8$ is F, then the remaining two of $R_5$, $R_6$, $R_7$, and $R_8$ are the same and linked to the same carbon atom; and further with the proviso that when $R_5$ and $R_7$ together with the carbon to which they are attached, or $R_6$ and $R_8$ together with the carbon atom to which they are attached, are linked to form a cyclic then one of the remaining two of $R_5$, $R_6$, $R_7$, and $R_8$ is F and the other is selected from H, Cl, Br, and I.

2. The process of claim 1 wherein the second olefin is reacted with hypofluorite in place of first olefin and the first intermediate hypofluorite is then reacted with the first olefin.

3. The process of claim 1 wherein the contacting is in a continuous process in which the mole amount of hypofluorite contacted is equal to or greater than the mole amount of first olefin $R_1R_2C=R_3R_4$ contacted and further wherein the residence time in the reactor is between about 0.05 and about 120 seconds, the temperature is between about −40° and about −150° C., and the first intermediate hypofluorite of the reaction of the first olefin with hypofluotite is continuously reacted with the second olefin.

4. A process according to claim 1 wherein the concentration of second olefin $R_5R_6C^2=C^1R_7R_8$ is constant and greater than about 0.01M and the temperature is between about −20° C. to −100° C.

5. The process of claim 4 wherein the concentration of second olefin is equal to or greater than about 3M.

6. In a process for making a fluorovinyl ether of structure:

$$CFX=CXOCF_2OR \qquad (I)$$

wherein:

1) R is a $C_2$–$C_6$ linear or branched perfluoroalkyl group, a $C_5$–$C_6$ cyclic perfluoroalkyl group, or a linear or branched perfluorooxyalkyl group comprising 2 to 6 carbon atoms and 1 to 3 oxygen atoms;

2) up to two fluorine atoms of the perfluoroalkyl group or the perfluorooxyalkyl group can be independently replaced with an atom selected from the group consisting of H, Cl, Br, and I; and 3) X is F or H;

the step of:

contacting a first fluoroalkene with a hypofluorite to form a first intermediate; then contacting the first intermediate with a second fluoroalkene to form a second intermediate;

1) the hypofluorite is of structure $X_1X_2C(OF)_2$ wherein $X_1$ and $X_2$ are the same or different and selected from F and $CF_3$; and 2) the first and second fluoroalkenes may be the same or different and are selected from $R^A_1R^A_2C=CR^A_3R^A_4$ and $R^A_4R^A_5C=CR^A_7R^A_8$ wherein each of $R^A_1$, $R^A_2$, $R^A_3$, $R^A_4$, $R^A_5$, $R^A_6$, $R^A_7$, and $R^A_8$ are the same or different and are selected from the group consisting of H, F, Cl, Br, I, —$CF_2OSO_2F$, —$SO_2F$, —$C(O)F$, $C_1$–$C_5$ linear or branched perfluoroalkyl, and linear or branched oxyperfluoroalkyl.

* * * * *